US00PP29231P3

(12) United States Plant Patent
Klemm et al.

(10) Patent No.: US PP29,231 P3
(45) Date of Patent: Apr. 10, 2018

(54) ***OSTEOSPERMUM* PLANT NAMED 'KLEOE15272'**

(50) Latin Name: *Osteospermum ecklonis*
Varietal Denomination: KLEOE15272

(71) Applicant: Klemm+Sohn GmbH & Co. KG, Stuttgart (DE)

(72) Inventors: Nils Klemm, Stuttgart (DE); Silke Wagener, Leinfelden-Echterdingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/530,208

(22) Filed: Dec. 12, 2016

(65) Prior Publication Data

US 2017/0290242 P1 Oct. 5, 2017

(30) Foreign Application Priority Data

Mar. 30, 2016 (QZ) ..... PBR 2016/0849

(51) Int. Cl.
*A01H 5/02* (2018.01)

(52) U.S. Cl.
USPC ..... Plt./360
CPC ..... *A01H 5/025* (2013.01)

(58) Field of Classification Search
USPC ..... Plt./360
CPC ..... A01H 5/025
See application file for complete search history.

(56) References Cited

PUBLICATIONS http://www.balllandscape.com/pdf/Selecta-2016Catalog-15117.pdf; 2015; 126 pages.*

* cited by examiner

*Primary Examiner* — Kent L Bell
(74) *Attorney, Agent, or Firm* — Barbara Campbell; Bethany R. Roahrig; Cochran Freund & Young LLC

(57) ABSTRACT

A new *Osteospermum* plant particularly distinguished by ray florets having light purple tips and white centers and a semi-upright growth habit, is disclosed.

1 Drawing Sheet

Genus and species: *Osteospermum ecklonis.*
Variety denomination: 'KLEOE15272'.

CROSS REFERENCE TO RELATED APPLICATION

The current application claims the benefit of priority to Community Plant Variety Rights application number 2016/0849, as filed on Mar. 30, 2016, the entire contents of which are incorporated herein by reference.

BACKGROUND OF THE NEW PLANT

The present invention comprises a new and distinct variety of *Osteospermum*, botanically known as *Osteospermum ecklonis*, and hereinafter referred to by the variety name 'KLEOE15272'. 'KLEOE15272' originated from a cross-pollination conducted in summer 2011 in Nairobi, Kenya between the proprietary female *Osteospermum* variety 'OE-2002-V 034' (unpatented), and the male *Osteospermum* variety Brandkamp 'White Pink Tips' (patent status unknown).

The seeds from the cross were sown and plants were grown in a greenhouse for evaluation, where an individual plant designated 'KLEOE15272' was selected from the group of plants in spring 2012. In spring 2012, 'KLEOE15272' was first vegetatively propagated by terminal vegetative cuttings. 'KLEOE15272' was found to reproduce true to type in successive generations of asexual propagation via terminal vegetative cuttings.

SUMMARY

The following are the most outstanding and distinguishing characteristics of this new variety when grown under normal horticultural practices in Stuttgart, Germany.

1. Ray florets having light purple tips with white centers; and
2. A semi-upright growth habit.

DESCRIPTION OF THE PHOTOGRAPH

This new *Osteospermum* plant is illustrated by the accompanying photograph which shows the plant's overall plant habit including form, foliage, buds, and inflorescences. The photograph is of a four-month-old plant grown in a greenhouse in Stuttgart, Germany in April 2014. The colors shown are as true as can be reasonably obtained by conventional photographic procedures.

DESCRIPTION OF THE NEW VARIETY

The following detailed descriptions set forth the distinctive characteristics of 'KLEOE15272'. The data which define these characteristics were collected from asexual reproductions carried out in Stuttgart, Germany. Data was collected on four-month-old plants grown in a greenhouse in Stuttgart, Germany in June 2016. Color references are to The R.H.S. Colour Chart of The Royal Horticultural Society of London (R.H.S.), 5th edition (2007).

Classification:

*Family*.—Asteraceae.

*Botanical*.—*Osteospermum ecklonis*.

*Common*.—*Osteospermum*.

*Designation*.—'KLEOE15272'.

Parentage:

*Female parent*.—The proprietary female *Osteospermum* variety 'OE-2002-V 034' (unpatented).

*Male parent*.—The male *Osteospermum* variety Brandkamp 'White Pink Tips' (patent status unknown).

Plant:

*Form and habit*.—Herbaceous perennial but usually cultivated as an annual.

*Growth habit*.—Semi-upright.

*Branching habit*.—Freely-branching.

*Height* (*from top of soil, including inflorescence*).—About 25.0 cm.

*Width* (*including inflorescences*).—30.0 cm to 40.0 cm.

*Propagation*.—Terminal cuttings.

*Time to produce a finished flowering plant*.—10 weeks.

*Time to initiate and develop roots*.—About 3 weeks.

*Root description*.—Freely-rooting, light tan in color.

Leaves:

*Arrangement*.—Alternate.

*Shape*.—Dentiform.

*Apex*.—Obovate.

*Base*.—Acute.

*Margin*.—Serrate.

*Immature color*.—Upper surface: RHS 143A. Lower surface: RHS 143A.

*Mature color*.—Upper surface: RHS 141A. Lower surface: RHS 141B.

*Length*.—8.0 cm.

*Width*.—3.0 cm.

*Texture and appearance* (*upper and lower surfaces*).—Leathery and shiny, with a covering of fine hairs.

*Petioles*.—Absent.

*Venation patter*.—Pinnate.

*Venation color*.—Upper surface: RHS 143C. Lower surface: RHS 143C.

Stems:

*Total number of branches per plant* (*calculated at the base of the plant*).—About 5 main branches.

*Length*.—Up to 15.0 cm.

*Diameter*.—0.7 cm.

*Internode length*.—1.0 cm to 2.0 cm.

*Color*.—RHS 144B.

*Texture*.—Smooth.

*Anthocyanin*.—Absent.

Flower buds:

*Shape*.—Round-ovoid.

*Length*.—About 1.0 cm.

*Diameter*.—About 1.0 cm.

*Color* (*at tight bud just before the ray florets unfold*).—RHS 143A.

Inflorescence:

*Type*.—Composite, single.

*Blooming habit*.—Spring to autumn.

*Quantity of inflorescences per plant*.—30 to 40.

*Lastingness of the inflorescences on the plant*.—About 2 weeks.

*Fragrance*.—Absent to faint.

*Inflorescence diameter*.—7.0 cm.

*Inflorescence depth*.—1.0 cm.

*Disc diameter*.—1.0 cm.

Disc floret:

*Quantity per inflorescence*.—About 50.

*Shape*.—Oblanceolate.

*Tube color*.—Closed: RHS 97A. Mature and inner surface: RHS N88D.

*Length*.—About 0.5 cm.

*Diameter* (*at apex*).—About 0.1 cm to 0.3 cm.

*Apex*.—Obtuse.

*Apex color*.—RHS N88D.

*Base*.—Acute.

*Base color*.—RHS 155C.

*Margin*.—Entire.

Ray floret:

*Quantity per inflorescence*.—About 20.

*Shape*.—Lanceolate.

*Color*.—Upper surface: RHS 75A tips and RHS NN155A centers. Lower surface: Stripes of RHS 97A and RHS 97D with shades of RHS 75A.

*Length*.—Up to 3.0 cm.

*Width*.—About 1.0 cm.

*Apex*.—Obtuse.

*Base*.—Acute.

*Margin*.—Entire.

*Texture*.—Upper surface: Smooth. Lower surface: Smooth.

Peduncle:

*Length*.—Up to 9.0 cm.

*Diameter*.—0.2 cm.

*Texture*.—Covered with fine hairs.

*Color*.—RHS 143B.

Phyllaries:

*Texture*.—Rough with fine hairs.

*Arrangement*.—Single.

*Observed quantity per plant*.—About 20.

*Shape*.—Lanceolate.

*Color*.—Upper surface: RHS 143B. Lower surface: RHS 143C.

*Length*.—About 1.0 cm.

*Width*.—0.2 cm.

*Apex*.—Narrowly acute.

*Base*.—Acute.

*Margin*.—Entire.

*Texture*.—Upper surface: Shiny. Lower surface: Covering of fine hairs.

Reproductive organs:

*Androecium*.—Location: On the disc floret. Stamens: Quantity: 100 to 120. Shape: Filamentous. Filament length: About 0.4 cm. Filament diameter: Less than 0.05 cm. Anther: Shape: Lanceolate. Color: RHS N92A. Length: About 0.2 cm. Diameter: Less than 0.05 cm. Pollen: Color: RHS 14A. Amount: Moderate.

*Gynoecium*.—Location: On the base of the ray florets, reduced on disc florets. Pistils: Number: About 20 per inflorescence. Length: About 0.5 cm. Diameter: Less than 0.05 cm. Stigma: Color: RHS N79A. Shape: Oval. Length: Greater than 0.1 cm. Diameter: Greater than 0.1 cm. Style: Color: RHS 76B. Length: About 0.3 cm. Diameter: 0.05 cm.

Fruit and seed set: None observed.

Disease and pest/insect resistance: No disease and pest/insect resistance observed.

COMPARISON WITH PARENTAL LINES AND KNOWN VARIETY

'KLEOE15272' is distinguished from its parents, the female parent 'OE-2002-V 034' (unpatented) and the male parent, Brandkamp 'White Pink Tips' (patent status unknown), as described in Table 1.

TABLE 1

Comparison with Parental Lines

| Characteristic | 'KLEOE15272' | Female Parent 'OE-2002-V 034' | Male Parent Brandkamp 'White Pink Tips' |
|---|---|---|---|
| Ray floret color | Light purple tips | Pink and lighter in the center | White-pink tips |

'KLEOE15272' is most similar to the commercial *Osteospermum* variety 'KLEOE05115' (U.S. Plant Pat. No. 18,634). Differences between the varieties are described in Table 2.

TABLE 2

Comparison with Similar Variety

| Characteristic | 'KLEOE15272' | 'KLEOE05115' |
|---|---|---|
| Ray floret color | Light purple tips | Light violet and darker at the base |

We claim:

1. A new and distinct variety of *Osteospermum* plant named 'KLEOE15272' as illustrated and described herein.

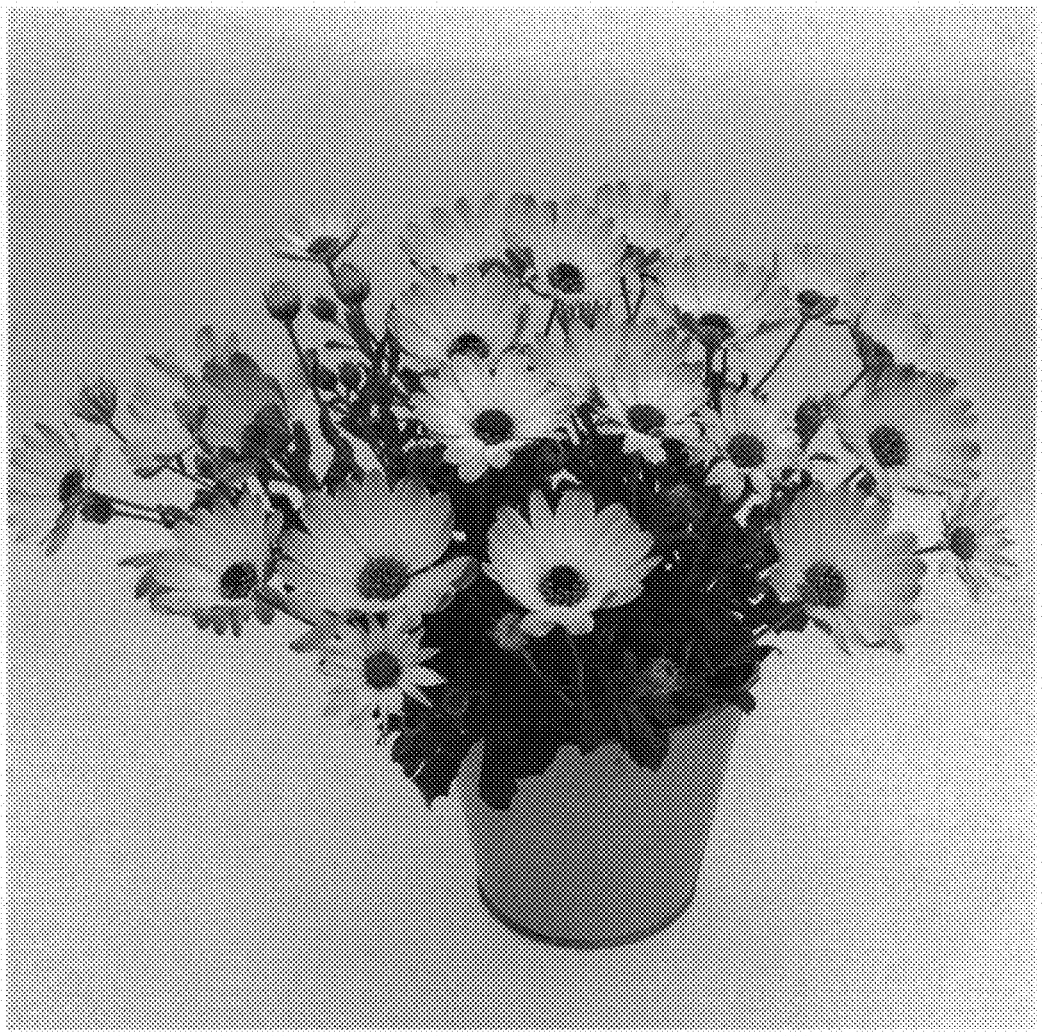

* * * * *